(12) United States Patent
Peipsi et al.

(10) Patent No.: US 10,568,561 B2
(45) Date of Patent: Feb. 25, 2020

(54) SYSTEM AND METHOD FOR NON-INVASIVE MEASUREMENT OF SOFT BIOLOGICAL TISSUE

(71) Applicant: MYOTON AS, Tallinn (EE)

(72) Inventors: Aleko Peipsi, Tallinn (EE); Mart Liik, Tallinn (EE); Anti Sullin, Tallinn (EE)

(73) Assignee: MYOTON AS, Tallinn (EE)

( * ) Notice: Subject to any disclaimer, the term of this patent is extended or adjusted under 35 U.S.C. 154(b) by 644 days.

(21) Appl. No.: 14/766,295

(22) PCT Filed: Jan. 21, 2014

(86) PCT No.: PCT/EP2014/051154
§ 371 (c)(1),
(2) Date: Aug. 6, 2015

(87) PCT Pub. No.: WO2014/122011
PCT Pub. Date: Aug. 14, 2014

(65) Prior Publication Data
US 2015/0374275 A1    Dec. 31, 2015

(30) Foreign Application Priority Data
Feb. 6, 2013 (GB) .................................. 1302093.8

(51) Int. Cl.
*A61B 5/00* (2006.01)
*G01N 3/42* (2006.01)

(52) U.S. Cl.
CPC ............ *A61B 5/442* (2013.01); *A61B 5/0053* (2013.01); *A61B 5/4519* (2013.01);
(Continued)

(58) Field of Classification Search
None
See application file for complete search history.

(56) References Cited

U.S. PATENT DOCUMENTS 6,132,385 A    10/2000 Vain
2008/0221484 A1*    9/2008 Sarvazyan ............. A61B 5/103
600/587

(Continued)

FOREIGN PATENT DOCUMENTS

EE      201000094    *    7/2011    ............. A61B 5/103
WO      97035521 A1    10/1997
(Continued)

OTHER PUBLICATIONS

Patents Act 1977: Search Report under Section 17(5), dated Jun. 25, 2013 for Application No. GB1302093.8.
(Continued)

*Primary Examiner* — Sean P Dougherty
*Assistant Examiner* — Benjamin S Melhus
(74) *Attorney, Agent, or Firm* — Heslin Rothenberg Farley & Mesiti P.C.; Victor A. Cardona, Esq.

(57) ABSTRACT

A system and method for the non-invasive measurement of tone, state of tension, biomechanical or viscoelastic properties of soft biological tissues includes a testing-end, an actuator arranged to apply a force to the testing-end, and a sensor to sense movement of the testing-end. A signal generating circuit supplies a control signal to the actuator so the biological tissues are subjected by the testing-end to a load, including means to adjust the signal provided by the signal generating circuit in accordance with the component of weight acting through the testing-end onto the biological tissue so that the load to which the biological tissue is subjected is constant. An impulse signal generating circuit supplies an impulse signal to the actuator so the biological tissue is subjected by the testing-end to a mechanical deformation. In use the soft biological tissue is subjected first to the constant load, and then to the impulse signal; and the
(Continued)

consequent movement of the biological tissue is then registered.

14 Claims, 3 Drawing Sheets

(52) U.S. Cl.
CPC ............ *A61B 5/4523* (2013.01); *G01N 3/42* (2013.01); *G01N 2203/0089* (2013.01)

(56) References Cited

U.S. PATENT DOCUMENTS

| | | |
|---|---|---|
| 2011/0054355 A1 | 3/2011 | Hunter |
| 2012/0053440 A1 | 3/2012 | Chardon |
| 2015/0005679 A1* | 1/2015 | Becse ............ A61B 17/22004 601/15 |

FOREIGN PATENT DOCUMENTS

| | | |
|---|---|---|
| WO | 98008073 A1 | 2/1998 |
| WO | 20120089221 A1 | 7/2012 |
| WO | 20130156415 A1 | 10/2013 |

OTHER PUBLICATIONS

International Search Report dated May 20, 2014 for International Application No. PCT/EP2014/051154.

\* cited by examiner

SYSTEM AND METHOD FOR NON-INVASIVE MEASUREMENT OF SOFT BIOLOGICAL TISSUE

CROSS REFERENCE TO RELATED APPLICATIONS

This application is a national stage filing under section 371 of International Application No. PCT/EP2014/051154, filed on Jan. 21, 2014, and published in English on Aug. 14, 2014, as WO 2014/122011 A1, and claims priority of Great Britain application No. 1302093.8 filed on Feb. 6, 2013, the entire disclosure of these applications being hereby incorporated herein by reference.

FIELD OF INVENTION

The present invention relates to the field of medical diagnostic technologies, more precisely to the field of methods and devices for the non-invasive measurement of tone, biomechanical and viscoelastic properties of skin, muscles, tendons and other soft biological tissues.

The dynamic measurement method consists of the registration of a damped oscillation of a soft biological tissue after the exertion of an external, light, quick-released mechanical impulse under constant pre-compression.

A constant pre-compression of the subcutaneous layer is imperative in the dynamic measurement of soft biological tissue. Without application of a constant pre-compression, the non-invasive measurement method would not be possible as the pre-compressed layer above the muscle or tissue being measured acts as a bridge or a connection between the muscle and the testing-end of the medical diagnostic device. As a skeletal muscle is a very sensitive organ and has limitations in responding to an external mechanical impulse, the force of the pre-compression must be optimal and constant. If the pre-compression force over a given area is too small, it does not pre-compress the subcutaneous fat layer sufficiently, or the impulse does not reach the deeper layers and less oscillation mass of the muscle/tissue being measured will be involved, and furthermore, in case of higher stiffness and elasticity (as in a tendon) the testing-end jumps off the measurement surface when the tissue restores its shape after being deformed. If the pre-compression is too great, then the tissue's response is damped too much, and measurements of smaller or elderly muscles with lower elasticity may not be possible.

Soft biological tissues' characteristic behaviour with regard to stiffness and elasticity when deformed is not linear, unlike the linear response of many other non-biological materials (e.g. metals). This is also the reason why in the dynamic measurement method stiffness and logarithmic decrement (as an indication of elasticity) are derived directly from the oscillation acceleration, velocity or displacement instead of using a Young's modulus. When applying any mechanical measurement solution for soft tissue assessment, all physical or electrical factors which take part in causing the stimulation of a tissue must be optimised and standardised, and remain constant over time. Unless these factors are constant and standardised, the measurement results would be device-, manufacturer-, or user-dependant and therefore the measurement results would not be not comparable.

Measurement results depend or the following physical factors being standardised:
mechanical friction, inertia and weight of the measurement mechanism;
diameter of the testing-end (deformation area of the measurement surface);
force of pre-compression;
impulse force characteristics—amplitude, shape and duration;
characteristics of an actuator; and
operational temperature range.

State of the Art

There are several known technical solutions and methods for the non-invasive assessment of tone, biomechanical or viscoelastic properties of superficial skeletal muscles. These parameters are:
Tone—State of intrinsic tension without voluntary contraction—indicated by oscillation Frequency [Hz]
Biomechanical properties
Stiffness [N/m]
Elasticity—indicated by Logarithmic Decrement (without unit)
Viscoelastic properties
Creep—Deborah number (without unit)
Mechanical Stress Relaxation Time [ms]
Objective assessment and monitoring of the above-mentioned parameters enable the evaluation of the health and quality of function of superficial skeletal muscles.

Some non-invasive measurement solutions are:
MYOTONOMETER muscle stiffness meter http://www.neurogenic.com/pages/technical-info.php,
IMOTO muscle hardness meter PEK-1 http://www.imoto-ss.net/product/medical/PEK-1.html,
NEUTONE muscle hardness tester http://www.try-all-jpn.com/english/hardness_meter/index.html, where muscle resistance to the force of deformation is registered.
TENSIOMYOGRAPHY http://www.tmg.si/en/products/tmg-products/about-tensiomyography, where muscle response to an external electrical impulse is registered.
MYOTONOMETER, MOTO AND NEUTONE all utilise so called static measurement methods where the soft tissue resistance of displacement to the force of deformation is measured or registered statically.
TENSIOMYOGRAPHY utilises a combination of static and dynamic measurement methods: The static part of the method lies in the pre-compression of the tissue being measured and the dynamic part in an external electrical impulse and consequent registration of a muscle contraction.

The above-mentioned methods use a mechanical solution based on a translational Motion shaft in combination with a spiral spring in order to create and deliver the impulse to the skin surface above the muscle being measured with the testing-end of the device. The disadvantage in the above-mentioned solutions is that the force of deformation applied to the soft tissue may change over time due to the following factors: creep of a spiral spring, mechanical friction of the measuring mechanism, viscosity of the lubricant materials, stiffness and friction of the seal, or dirt particles on the sleeve-bearing or other type of bearings used in the measurement mechanism.

Furthermore it is imperative that a mechanical measurement system should have minimal friction and inertia. Relaxed skeletal muscles (unlike tendons) have very low ability to store and to recover mechanical energy through the pre-compressed subcutaneous layer, and such energy storage and recovery is required for any dynamic method. Even the smallest mechanical friction in the device measurement mechanism causes significant damping which results in poor sensitivity or even complete failure of the measurement.

A technical solution for a dynamic measurement method is described in U.S. Pat. No. 6,132,385 (A) "*Method and a device for recording mechanical oscillations in soft biological tissues*".

A clear advantage of this dynamic measurement method compared to the previous static ones is the registration of the oscillation in the form of an acceleration graph of any superficial soft tissue (not only muscles) over a very short duration. The oscillation graph obtained enables the simultaneous computation of three of the above-mentioned parameters (Tone, State of Tension, Stiffness and Logarithmic Decrement (as an indication of Elasticity)) of the tissue being measured in real-time. As the measurement time is very short (150 ms) the subject cannot affect the registration of the oscillation and therefore the measurement result, either voluntarily or involuntarily.

In this solution the pre-compression of the subcutaneous layer above the muscle being measured is caused by the weight of the device measuring mechanism. Therefore the solution creates the pre-compression farce only if measurements are performed exactly in a direction parallel to the gravity vector and the gravity force is constant. The main disadvantage of the U.S. Pat. No. 6,132,385 solution is that it is not possible to conduct consistent measurements if they have to be performed at any angle to the direction of the gravity vector. For example, if the measurement direction is horizontal or vertically upwards, then the pre-compression produced is respectively zero or negative. Other disadvantages are the high inertia of a pivoted double-arm lever and relatively high and unstable friction in the lever bearings.

A technical solution for the non-invasive dynamic measurement of a soft biological tissue is described in WO2012089221 (A1) "Device and method for real-time measurement of parameters of mechanical stress state and biomechanical properties of soft biological tissue". The solution comprises a frictionless, translational motion shaft system which makes the system more sensitive compared to the previous solutions.

A disadvantage of the solution described in WO2012089221 is that the oscillation of the Measurement mechanism is significantly affected by the force of gravity, if the measurement is taken when the Y-axis of the testis of the measurement mechanism is not parallel to the gravity vector. The mechanism is maximally affected by gravity when the X and Y-axes are perpendicular and the Z-axis is parallel to the gravity vector. This could result in measurement differences due to gravity that are statistically significant.

BRIEF DESCRIPTION OF THE INVENTION

The objective of the present invention is to provide a system and method for the non-invasive measurement of tone and biomechanical and viscoelastic properties of soft biological tissues, which can provide for a constant pre-compression, with compensation for the weight of the measuring mechanism, an inclination detection system around the axis of the testing-end, as well as a system for the direct measurement of maximum displacement. The invention enables the mass of the measuring mechanism, and so its inertia, to be significantly reduced, so that measurements are a more accurate reflection of the state of tension or the properties of the soft tissues that are being measured.

The system and method described in this present invention together with the frictionless measurement mechanism incorporated from WO2012089221 (A1) enable the simultaneous, consistent and reliable measurement of tone, state of tension, biomechanical and viscoelastic properties of skin, muscles, tendons and other soft biological tissues in vivo, in real time at any angle to the direction of the gravity vector as well as in the environmental conditions of microgravity.

According to the present invention there is provided a system for the non-invasive measurement of tone, state of tension, biomechanical and viscoelastic properties of soft biological tissues comprising a testing-end, an actuator arranged to apply a force to the testing-end, and a sensor to sense movement of the testing-end, wherein the system comprises a signal generating circuit to supply a control signal to the actuator so the biological tissues are subjected by the testing-end to a load, including means to adjust the signal provided by the signal generating circuit in accordance with the component of weight acting through the testing-end onto the biological tissues so that the load to which the biological tissues are subjected has a pre-set value; and an impulse signal generating circuit to supply an impulse signal to the actuator so the biological tissues are subjected by the testing-end to a mechanical impulse.

The present invention ensures that a constant pre-compression force is delivered by the device testing-end to the skin surface regardless of the measurement direction in order to pre-compress the subcutaneous layer above the tissue being measured. The testing-end of a device may be placed perpendicular to the measurement surface over a tissue being measured.

The present invention comprises a weight compensation system such that if the mass of the measuring mechanism is changed, then the compensation mechanism enables the same pre-compression force to be retained in all directions in gravity in spite of the consequent change in weight of the measuring mechanism.

The advantages of the system and method of the present invention are as follows. The system can be used in any frictionless soft tissue diagnostic solution where pre-compression of the subcutaneous layer is the essential part of the dynamic measurement method and where physical contact with the skin surface above the tissue being measured is imperative. Both these conditions are necessary in order to deliver to the tissue being measured the force of pre-compression as well as register the tissue's reaction to the external mechanical or electrical impulse. The system may be used for the dynamic measurement method of the above-mentioned parameters in a gravitational field, as well as in microgravity. It will be appreciated that direct measurement of the maximum displacement (required for the computation of Stiffness) by utilisation of a position or displacement sensor has higher accuracy than when the displacement is derived from the oscillation acceleration signal. A benefit of the short duration of the mechanical deformation impulse (e.g. 15 ms), is that the maximum deformation of a soft tissue takes place only a few milliseconds after the end of the deformation impulse. Therefore the maximum displacement is registered before the opposite movement of the device and potential neurological reaction of a skeletal muscle or other tissue being measured. This leads to the situation where the reference starting point is not needed, as required in previously described static measurement solutions, and the instant of registration of the measurement is not influenced by the subject. Furthermore as a disc-like mechanical item around the testing-end for the reference starting point is not required (such as the 30 mm disc in the case of the Myotonometer), the measurement position on the skin surface can be seen, so that smaller tissues can be measured more precisely.

The pre-compression is:
calibrated as required to account for differences in the components used, and small weight differences of the measuring mechanism,
constant over time,
objective and automatically controlled by the system,
independent from the user,
independent of slight differences in the force of gravity on Earth, and
independent of direction of measurement and the gravity vector.

BRIEF DESCRIPTION OF THE DRAWING

The present invention is explained more precisely with reference to the figures attached, by way of example only, in which.

DETAILED DESCRIPTION OF THE INVENTION

Figure 1:
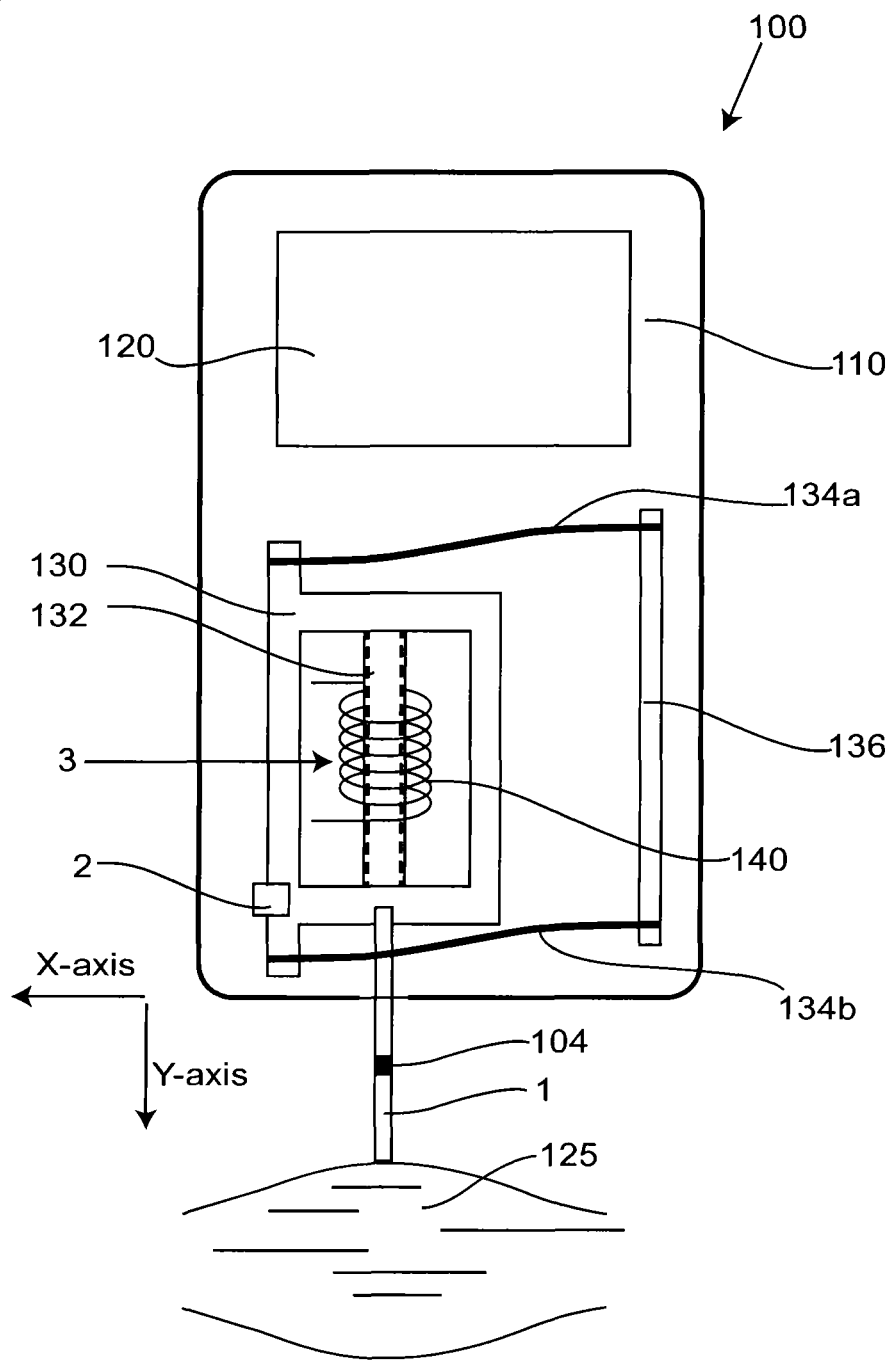
FIG. 1 shows a schematic view of a sensing instrument of the invention.

Referring to FIG. 1, a sensing instrument 100 comprises a housing 110 enclosing electronics 120, and defining an aperture through which projects a rod or testing-end 1 which may be held against the soft tissue 125. The testing-end 1 is attached to a rectangular frame 130 which includes a magnetic core 132. The frame 130 is supported resiliently within the housing 110 by thin leaf springs 134a and 134b at opposite ends which are supported at their other ends by a bar 130 which is fixed to or integral with the housing 110. Any movement of the frame 130 can be detected by a sensor 2, which in this embodiment is a three-axis accelerometer mounted on the frame 130. The magnetic core 132 locates within a drive coil 140, so that a current provided to the drive coil 140 causes the magnetic core 132 to move, so constituting an actuator 3, so moves the testing-end 1 along its own longitudinal axis. The end of the testing-end 1 which is to contact the soft tissue 125 may for example be circular, and of diameter 3 mm, when taking measurements of thin muscles, or particularly compliant soft tissues, it may be desirable to provide a larger diameter tip to the testing-end 1, for example of diameter 5 mm, 6 mm, 8 mm, or 10 mm.

The longitudinal axis of the testing-end 1 may be referred to as the Y-axis. The X-axis is parallel to a plane defined by two leaf springs 134a and 134b at opposite ends of the frame 130, and so is in the plane of FIG. 1; and the Z-axis is orthogonal to the plane defined by those two leaf springs 134a and 134b.

Figure 2:
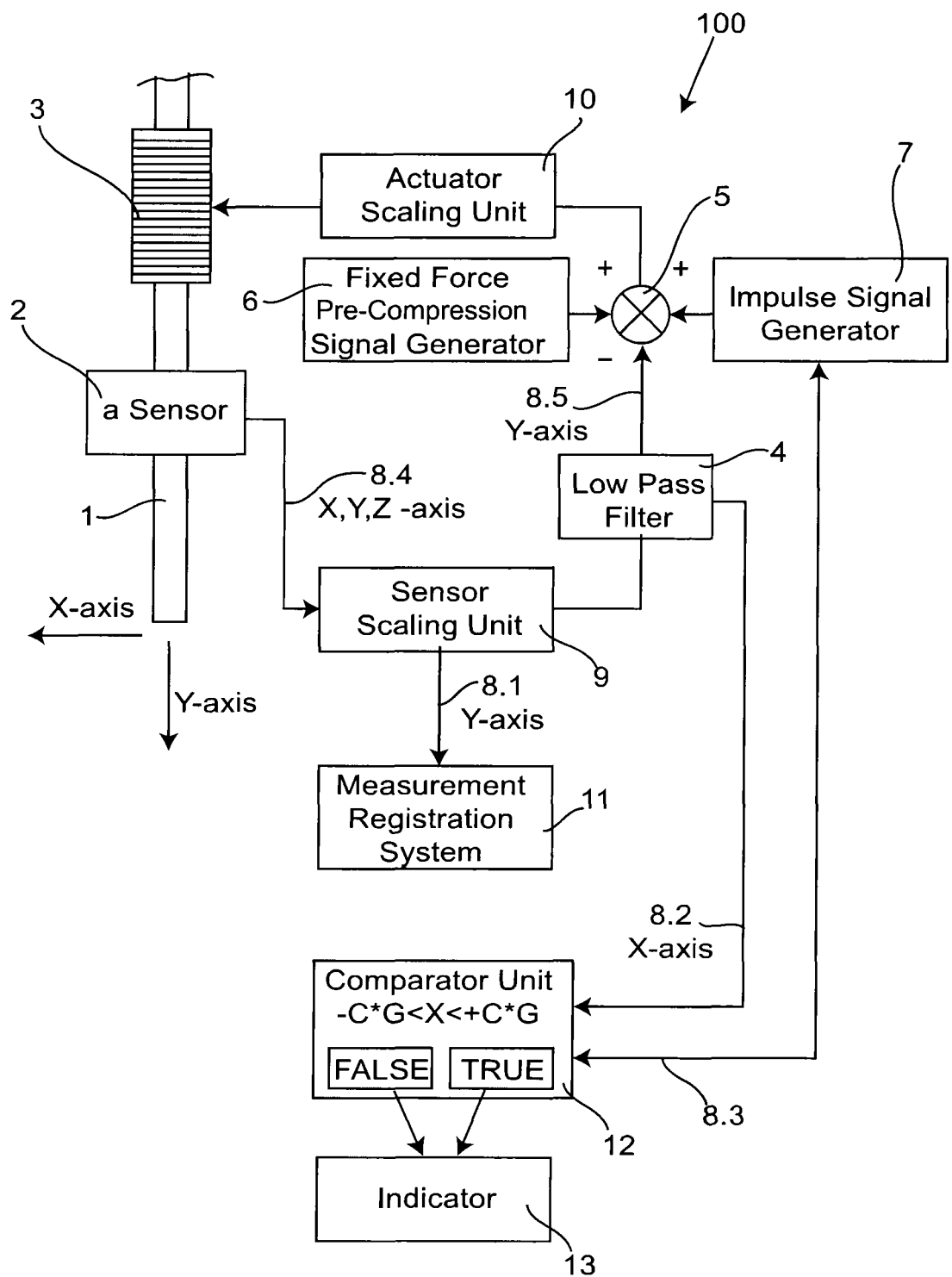
FIG. 2 shows a schematic view of details of the sensing instrument of FIG. 1, for the constant pre-compression, weight compensation and inclination prevention system in the dynamic measurement method.

Referring now to FIG. 2, this shows the testing-end 1, the sensor 2 and the actuator 3 schematically, and shows the electronics 120 as a block diagram. The signals 8.4 from the sensor 2, which represent the three components X, Y and Z of acceleration or gravity as digital signals, are supplied to a sensor scaling unit 9. The scaling unit 9 identifies possible off-sets of the signals, and may also amplify the signals by constant scaling factors, which we determined during the calibration of the instrument 100. The scaled Y-axis signal component 8.1 is supplied to a measurement registration system 11, providing a signal output from which the state of tension, biomechanical and viscoelastic properties of the soft tissue 125 can be calculated. The measurement registration system 11 also analyses the signal, subjecting it to signal processing for example to eliminate low and high frequencies which are not characteristic of a soft tissue damped oscillation, and to determine maximum and minimum extremes necessary for the calculations. The various parameters are computed and stored within the measurement registration system 11 of the instrument 100. The calculated parameters from individual or multiple measurements, or the oscillation signal, may for example be provided to a portable computer (not shown) for further analysis.

The scaled signals are then provided to a low pass filter 4. The low pass filter 4 provides an output signal 8.2 representing the component of acceleration or gravitational field in the X-direction, which is supplied to a comparator unit 12; and provides an output signal 8.5 representing the component of acceleration or gravitational field in the Y-direction, which is supplied as one input to a summing unit 5. The summing unit 5 is also provided with signals from a fixed force pre-compression signal generator 6 and from an impulse signal generator 7. The signal generator 6 provides a signal which corresponds to a fixed force, which is the desired pre-compression force to be applied by the testing-end 1 to the soft tissue 125. The signal from the impulse signal generator 7 corresponds to an impulse force to be applied by the testing-end 1 to the soft tissue 125, having a predetermined time variation. The signals from the signal generators 6 and 7 are added by the summing unit 5, whereas the signal 8.5, which corresponds to the component of the weight acting parallel to the Y-axis on the testing-end 1, is subtracted by the summing unit 5. The output from the summing unit 5 is supplied through an actuator scaling unit 10 to the coil 140 the actuator 3.

During calibration of the instrument 100 the scaling factor to be applied by the actuator scaling unit 10 is adjusted, with the instrument 100 held with the Y-axis parallel to the gravity vector but the instrument 100 upside down (in comparison to the orientation shown in the figures) and with a digital signal provided to the scaling unit 10, such that the actuator 3 just balances the weight of the measuring mechanism.

In use to take measurements, it will be appreciated that the summing unit 5 continuously adjusts the signal applied to the actuator scaling unit 10, and so to the actuator 3, in accordance with the orientation of the instrument 100, as represented by the signal 8.5, and so in accordance with the orientation of the Y-axis in relation to the gravity vector. This ensures that during any measurements the pre-compression force has a constant value applied to the actuator scaling unit 10 and so the actuator 3.

The comparator unit 12 compares the signal 8.2, corresponding to the component of the gravity perpendicular to the X-axis, to predetermined limits. As long as the signal is between those predetermined limits, which may correspond to plus or minus a fraction C of the gravitational field strength G, then the comparator unit 12 provides a signal 8.3 which enables the impulse signal generator 7 to provide an output. The comparator unit 12 also provides corresponding signals to an indicator 13 which may also provide an illuminated display, indicating if the signal is between the limits. For example the fraction C may be 0.1 or 0.2. Hence if the instrument 100 is inclined too far, leading the X-axis too far from being perpendicular to the gravity vector, measurements cannot be made. In one example the maximum angle of inclination of the X-axis may be 15°.

The Purpose of the Components

In use of the instrument 100, the instrument case 110 is held with the testing-end 1 against the skin surface above the soft tissue 125 being measured and pushed against the skin surface until a predetermined portion of the testing-end 1 projects. This may be marked by a marker 104 on the testing-end 1 (as shown in FIG. 1), and this is the position in which the leaf springs 134a and 134b are at their unstained state; this positioning does not have to be exact, and the tolerance may for example be plus or minus 1.5 mm. This position is the measurement position. When the position is correct, within this tolerance, this may be indicated by the indicator 13. The fixed force signal generator 6 provides its signal such that the forces acting on the testing-end 1 in the Y-direction are subsequently the component of the weight of the frame 130 (including that of the core 132 and of the testing-end 1) parallel to the Y-axis, and the force corresponding to the signal from the fixed force signal generator 6, after subtraction of the signal 8.5 representing the component of gravity parallel to the Y-axis. These two forces provide the required constant pre-compression force on the soft tissue 125.

When a constant state of pre-compression is achieved, an impulse signal is provided the impulse signal generator 7, which subjects the testing-end 1 and so the soft tissue 125 to a brief additional mechanical force. The soft tissue 125 undergoes a damped oscillation, so causing the testing-end 1 to undergo the same oscillation, and the sensor 2 enables the oscillation to be registered. In this example the oscillation is registered by recording the acceleration to which the testing-end 1 is subjected by the soft tissue 125. The measurement registration system 11 therefore receives digital signals representing this acceleration. It will be appreciated that the displacements of the testing-end 1 can be deduced by integrating the acceleration signals 8.1 twice.

The sensor scaling unit 9 compensates the X, Y and Z-axis components of acceleration for any signal off-set errors and for sensitivity of the sensor 2. The axes off-set and gain error parameters are setup as the result of the calibration process. Sensor scaling unit 9 computes the gravity compensation value according to the signals of acceleration sensor 2, delivers the X-axis component 8.2 to the comparator unit 12, the signal 8.5 representing the Y-axis component of gravitational field to the summing unit 5 (for the weight compensation purpose) and the X-axis component 8.1 of the measurement signal to the measurement registration system 11. The Z-axis component together with the X and Y-axis component may also be used for the computation of orientation of the measurement mechanism in the permanent gravity field or for the computation of the movement related total gravity force and its direction when a soft tissue oscillation or maximum displacement is registered.

The force actuator 3 generates the force of pre-compression and the force of the mechanical impulse. The low pass filter 4 filters out the Y-axis measurement signal related higher frequencies and provides clean X, Y and Z-axis components of the permanent gravity acceleration signals. The summing unit 5 sums the pre-determined fixed force pre-compression signal 6 and subtracts the Y-axis component of the permanent gravity acceleration signal 8.5 from the low pass filter 4. The impulse signal generator 7 generates the impulse signal with pre-determined amplitude, shape and duration. The Y-axis component measurement signal 8.1 is used for the computation of the measurement parameters. Actuator scaling unit 10 calibrates the actuator gain in order to ensure equal force emission in different devices. Differences in force emission originate from possible differences in the components of construction. The measurement registration system 11 is the tissue reaction registration system. The comparator unit 12 checks whether the X-axis component of permanent gravity acceleration signal 8.2 is within the pre-determined limits. The indicator 13 gives a warning/information to a user whether the system is within or outside the pre-determined limits.

Inclination of the instrument 100 when measuring a soft tissue 125 such that the X-axis is not perpendicular to the gravity vector, is measured by the X-axis component of permanent gravity acceleration signal 8.2 of the sensor 2 before the measurement of a tissue can be taken. When the X-axis is perpendicular to the gravity vector then the acceleration signal value in the X-axis is zero. When the acceleration signal value of X-axis is not zero but is a value that does not exceed a pre-determined limit (C×G), then the orientation relative to the gravity vector is acceptable and the instrument 100 is able to conduct the measurement. If the value is not in the range of the pre-determined limits then measurement is not allowed until the instrument 100 is moved to a position within the pre-determined limits.

When a measurement is to be taken, the testing-end 1 may be placed perpendicular to the skin surface above the soft biological tissue 125 being measured (e.g. superficial skeletal muscle). The orientation of the surface determines the measurement direction in relation to the direction of the gravity vector. After applying constant pre-compression, as described above, the impulse signal from the impulse signal generator 7 is then added by the summing unit 5 to the resultant constant pre-compression signal and delivered to the actuator 3 through the actuator scaling unit 10. The actuator 3 delivers the constant pre-compression force as well as the impulse through the testing-end 1 to the measurement surface.

After the impulse is delivered and released quickly under constant pre-compression, the tissue 125 being measured responds immediately in the form of a damped oscillation, causing the co-oscillation of a) the tissue being measured, b) the pre-compressed subcutaneous layers above the tissue, c) the testing-end 1, d) the frame 130, and e) the sensor 2. The sensor 2 registers the tissue reaction and delivers the Y-axis component measurement signal 8.1 to the measurement registration system 11.

Since the pre-compression is provided partly by the weight of the frame 130, and partly by the actuator 3 in response to the signal from the fixed force pre-compression signal generator 6 via the summing unit 5, the mass of the frame 130 can be minimised without affecting the pre-compression. For example in a situation in which the desired pre-compression force is 0.18 Newtons (N), this might be provided by a frame of mass of X g, whose pre-compression force is therefore Y N, the remaining pre-compression frame being provided by the actuator 3 (0.18 N-Y N). It will also be appreciated that if the instrument 100 is in an orientation in which the weight is acting in the direction of the Y-axis, the force provided by the actuator 3 will automatically be adjusted to provide the desired pre-compression force by virtue of the signal 8.5 applied to the summing unit 5. For example if the instrument 100 is upside down as compared to that shown in FIG. 1, then the force provided by the actuator 3 will equal the force required for pre-compression plus the weight of the frame 130, whereas in the orientation shown in FIG. 1 the force provided by the actuator 3 is equal to the force required for pre-compression minus the weight of the frame 130. Hence the present invention enables the mass of the frame to be minimised. The reduction in inertia enables more representative measurements to be made of the oscillation of the soft tissue 125, as the mass of the frame 130 is then a smaller proportion of the total oscillating mass.

The instrument 100 is described above as incorporating an accelerometer 2 as a sensor. It will be appreciated that alternative sensors may be used. For example the movement of the testing-end 1 and of the associated frame 130 might be instead monitored by a sensor for speed, or for displacement or position, or by a load sensor.

Figure 3:
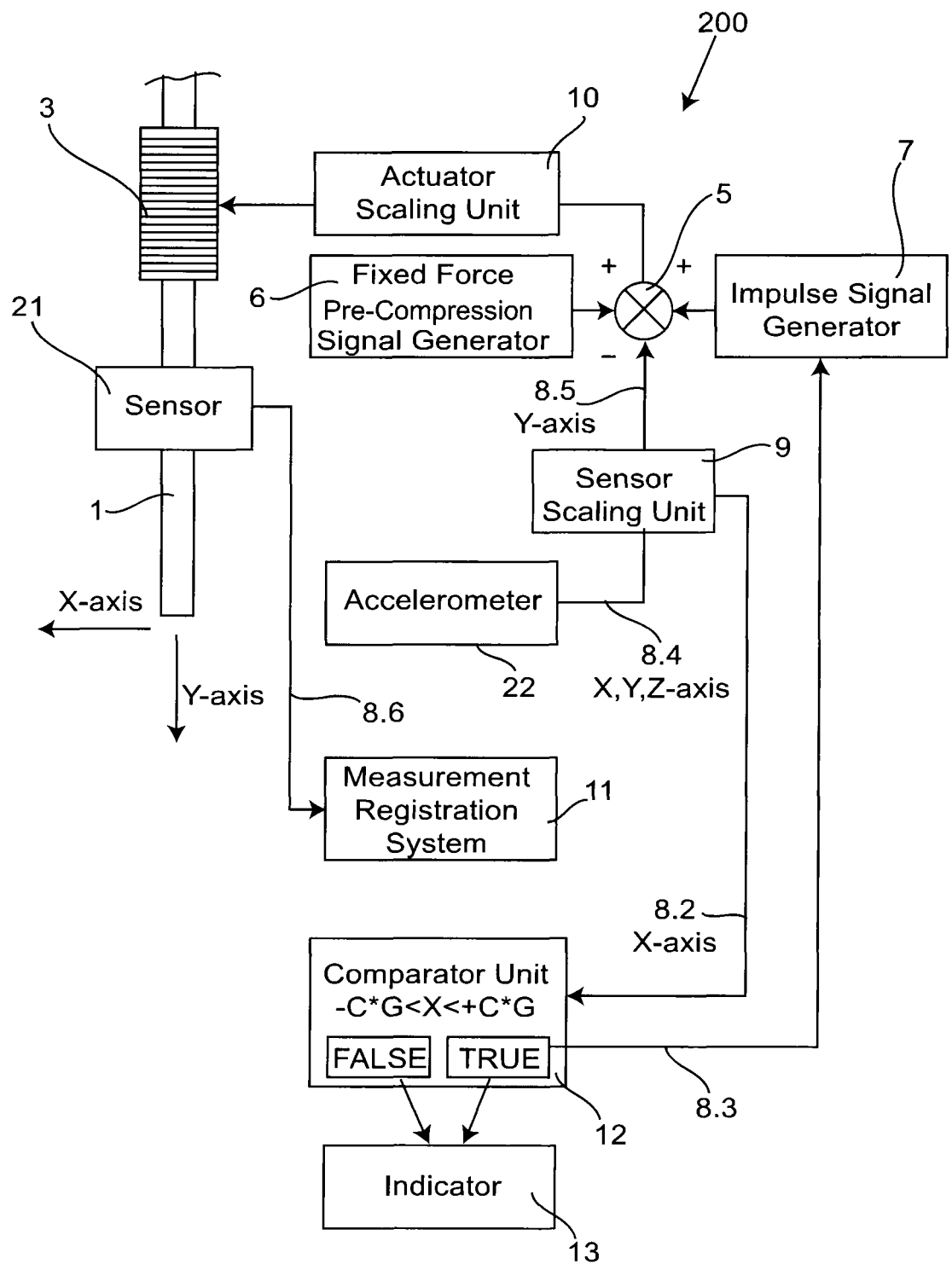
FIG. 3 shows a schematic view of a second embodiment, which is a modification of the embodiment of FIG. 2, but utilising two sensors.

Referring now to FIG. 3, a modified instrument 200 has many features in common with the instrument 100 described above. It differs in that the frame 130 carries a position sensor or a displacement sensor 21, providing an output signal 8.6 representing displacements of the testing-end 1 and of the frame 130. This signal may be provided directly to the measurement registration system 11. An accelerometer 22 is included within the electronics 120, but is not mounted on the frame 130. The signals 8.4 from the accelerometer 22 can be processed to account for off-sets and gains to be scaled by the sensor scaling unit 9, to provide signals representing the X-axis component of gravity 8.2, and representing the Y-axis component of gravity 8.5, as described in relation to the instrument 100.

In other respects the instrument 200 operates in the same way as described above in relation to the instrument 100. The instrument 200 is placed such that the testing-end 1 may be perpendicular to the skin surface above the soft biological tissue being measured (e.g. superficial skeletal muscle) and the instrument 200 is moved into position with the appropriate length of the testing-end 1 projecting (within the tolerance of ±1.5 mm). The pre-compression system creates the constant pre-compression to compress the subcutaneous tissue layer above the soft tissue 125, the actuator 3 in conjunction with the weight of the frame 130 providing the constant target force of deformation through the testing-end 1 to the tissue 125 being measured. The impulse signal generator 7 delivers the impulse signal to the actuator 3 through the summing unit 5 and the actuator scaling unit 10. The sensor 21 measures the displacement and delivers the result to the measurement registration system 11. The displacement is then used in the calculation of the properties such as stiffness of the tissue.

In a modification of the instrument 200, the frame 130 connected to the testing-end 1 may carry both the position sensor 21 and an acceleration sensor 2 as described in relation to FIG. 2.

The invention claimed is:

1. A system for the non-invasive measurement of tone, state of tension, biomechanical or viscoelastic properties of soft biological tissues comprising a testing-end movable along a Y-axis and supported resiliently within a housing by two parallel spaced-apart leaf springs, an actuator arranged to apply a force to the testing-end, and a sensor to sense movement of the testing-end, wherein the system comprises a signal generating circuit to supply a control signal to the actuator so the biological tissues are subjected by the testing-end to a pre-compression load, including means to adjust the control signal provided by the signal generating circuit in accordance with a component of weight acting through the testing-end onto the biological tissues so that the pre-compression load to which the biological tissues are subjected has a pre-set value; and an impulse signal generating circuit to supply an impulse signal to the actuator so the biological tissues are subjected by the testing-end to a mechanical impulse,
wherein the system comprises an accelerometer arranged to sense orthogonal components X and Y of the gravitational field relative to the testing-end, wherein the Y-axis is parallel to the direction of movement of the testing-end, and the X-axis is parallel to a plane defined by the two leaf springs, and to provide signals representing the Y-axis and the X-axis signal components, and a low-pass filter to process the signals representing the Y-axis and X-axis signal components to provide a compensating signal representing the Y-axis component of the gravitational field and a test signal representing the X-axis component of the gravitational field;
wherein the signal adjustment means is a summing unit, to which are provided the control signals from the signal generating circuit and the compensating signal representing the Y-axis component of gravitational field; wherein the summing unit is arranged to sum the control signal from the signal generating circuit, and to subtract the compensating signal representing the Y-axis component of gravitational field, to produce an output signal from the summing unit which is a pre-compression signal and which is provided to the actuator to provide a constant pre-compression load of the pre-set value independent of the orientation of the Y-axis;
wherein the test signal representing the X-axis component of the gravitational field is provided to a comparator, in which the test signal is compared to preset limits, and the comparator is arranged to provide an enabling signal to the impulse generating circuit as long as the test signal is between the preset limits;
and wherein, when an impulse is to be provided, the impulse generating circuit generates the impulse signal if it receives the enabling signal, the summing unit is provided with the impulse signal from the impulse generating circuit, the impulse signal being added by the summing unit to provide an output equal to the sum of the precompression signal and the impulse signal, and the output from the summing unit being provided to the actuator, so the mechanical impulse is delivered and released under the constant pre-compression load
wherein the compensating signal used to ensure a constant pre-compression load is based solely on the value of the signal representing the Y-axis component of the gravitational field, and wherein an enabling signal used to enable the impulse generating circuit is based on comparisons performed solely on the value of the test signal representing the X-axis component of the gravitational field.

2. A system as claimed in claim 1 wherein the sensor to sense movement of the testing-end is an accelerometer to produce signals representative of acceleration or gravitational field strength, and the low pass filter receiving signals derived from the accelerometer, and providing the compensating signal to the summing unit.

3. A system as claimed in claim 1, wherein the sensor comprises an accelerometer, position sensor, displacement sensor, speed sensor and/or a load sensor.

4. A system as claimed in claim 1 wherein the sensor to sense movement of the testing-end is a position or displacement sensor; and wherein the system also comprises an accelerometer to provide signals representative of gravitational field strength.

5. A system as claimed in claim 4 also comprising an accelerometer to sense movement of the testing-end.

6. A method for the non-invasive measurement of tone, state of tension, biomechanical or viscoelastic properties of soft biological tissues using a system comprising a testing-end movable along a Y-axis and supported resiliently within a housing by two parallel spaced-apart leaf springs, an actuator arranged to apply a force to the testing-end, and a sensor to sense movement of the testing-end, a signal generating circuit to supply a control signal to the actuator so the biological tissues are subjected by the testing-end to a pre-compression load, including means to adjust the control signal provided by the signal generating circuit in accordance with a component of weight acting through the testing-end onto the biological tissues so that the pre-compression load to which the biological tissues are subjected has a pre-set value; and an impulse signal generating circuit to supply an impulse signal to the actuator so the biological tissues are subjected by the testing-end to a mechanical deformation, wherein the system comprises an accelerometer arranged to sense orthogonal components X and Y of the gravitational field relative to the testing-end, wherein the Y-axis is parallel to the direction of movement of the testing-end, and the X-axis is parallel to a plane defined by the two leaf springs, and to provide signals representing the Y-axis and the X-axis signal components, and a low-pass filter to process the signals representing the Y-axis and X-axis signal components to provide a compensating signal representing the Y-axis component of the gravitational field and a test signal representing the X-axis component of the gravitational field; the signal adjustment means is a summing unit, to which are provided the control signals from the signal generating circuit and the compensating signal representing the Y-axis component of gravitational field;

the method comprising the following steps:

placing the system in a measuring initiation position with the testing-end in contact with the skin surface above the soft biological tissue being measured in which the springs are at their unstrained state;

arranging the signal generating circuit to supply the control signal through the summing unit to the actuator, the summing unit being arranged to sum the control signal from the signal generating circuit, and to subtract the compensating signal representing the Y-axis component of the gravitational field, to produce an output signal from the summing unit which is a precompression signal and which is provided to the actuator, so that the biological tissue is subjected to a constant pre-compression load of the pre-set value independent of the orientation of the Y-axis;

supplying the test signal representing the X-axis component of the gravitational field to a comparator, in which the test signal is compared to preset limits, the comparator being arranged to provide an enabling signal to the impulse generating circuit as long as the test signal is between the preset limits;

wherein the compensating signal used to ensure a constant pre-compression load is based solely on the value of the signal representing the Y-axis component of the gravitational field, and wherein the enabling signal used to enable the impulse generating circuit is based on comparisons performed solely on the value of the test signal representing the X-axis component of the gravitational field and, when an impulse is to be provided, arranging the impulse signal generating circuit to generate the impulse signal if it receives the enabling signal, and, to supply the impulse signal to the summing unit, the impulse signal being added by the summing unit to provide an output equal to the sum of the precompression signal and the impulse signal, and providing this output to the actuator so that the mechanical impulse is delivered and released under the constant pre-compression load; and sensing the resulting movement of the testing-end with the sensor, the component of movement parallel to a longitudinal axis of the testing-end being provided to a measurement registration system.

7. A method as claimed in claim 6 wherein the movement sensed by the sensor is acceleration.

8. A method as claimed in claim 6 wherein the accelerometer to provide the compensating signal is an accelerometer arranged to sense acceleration of the testing-end.

9. A method as claimed in claim 8 comprising filtering the signals from the accelerometer corresponding to a component of acceleration parallel to the Y-axis through a low pass filter.

10. A method as claimed in claim 6 wherein the accelerometer to provide the compensating signal is an accelerometer which is not arranged to sense acceleration of the testing-end.

11. A system as claimed in claim 1 wherein the preset limits are plus or minus a proportion of the gravitational field strength, and the proportion is selected from ±0.1 and ±0.2 times the gravitational field strength.

12. A system as claimed in claim 1 wherein the preset limits correspond to a maximum angle of inclination of the X-axis from the horizontal of 15°.

13. A method as claimed in claim 6 wherein the preset limits are plus or minus a proportion of the gravitational field strength, and the proportion is selected from ±0.1 and ±0.2 times the gravitational field strength.

14. A system as claimed in claim 13 wherein the preset limits correspond to a maximum angle of inclination of the X-axis from the horizontal of 15°.

\* \* \* \* \*